US011369603B2

United States Patent
Johns et al.

(10) Patent No.: US 11,369,603 B2
(45) Date of Patent: Jun. 28, 2022

(54) USE OF A H3R INVERSE AGONIST FOR THE TREATMENT OF SHIFT WORK DISORDER

(71) Applicant: Novartis AG, Basel (CH)

(72) Inventors: Donald Johns, Woburn, MA (US); Klaus Kucher, Basel (CH); Judit Sovago, Basel (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/605,240

(22) PCT Filed: Apr. 17, 2018

(86) PCT No.: PCT/IB2018/052655
§ 371 (c)(1),
(2) Date: Oct. 15, 2019

(87) PCT Pub. No.: WO2018/193372
PCT Pub. Date: Oct. 25, 2018

(65) Prior Publication Data
US 2020/0121679 A1 Apr. 23, 2020

(30) Foreign Application Priority Data
Apr. 19, 2017 (EP) .................................... 17166985

(51) Int. Cl.
*A61K 31/501* (2006.01)
*A61P 25/26* (2006.01)
*A61K 31/137* (2006.01)
*A61K 31/165* (2006.01)
*A61K 31/19* (2006.01)
*A61K 31/4458* (2006.01)
*A61K 31/522* (2006.01)

(52) U.S. Cl.
CPC .......... *A61K 31/501* (2013.01); *A61K 31/137* (2013.01); *A61K 31/165* (2013.01); *A61K 31/19* (2013.01); *A61K 31/4458* (2013.01); *A61K 31/522* (2013.01); *A61P 25/26* (2018.01)

(58) Field of Classification Search
CPC .................................................. A61K 31/501
See application file for complete search history.

(56) References Cited

U.S. PATENT DOCUMENTS

| | | | |
|---|---|---|---|
| 9,034,874 B2 * | 5/2015 | Auberson | A61K 31/496 514/252.02 |
| 9,273,026 B2 * | 3/2016 | Auberson | C07C 59/265 |
| 9,624,192 B2 * | 4/2017 | Auberson | C07C 59/265 |
| 2016/0158382 A1 | 6/2016 | Leonidov et al. | |

FOREIGN PATENT DOCUMENTS

| | | |
|---|---|---|
| WO | 2003032912 | 4/2003 |
| WO | 2004/058160 A2 | 7/2004 |
| WO | 2006103546 | 10/2006 |
| WO | 2006138604 | 12/2006 |
| WO | 2009/003003 A2 | 12/2008 |
| WO | 2009/105206 A1 | 8/2009 |
| WO | 2012170883 | 12/2012 |
| WO | 2013050987 | 4/2013 |
| WO | 2014013469 | 1/2014 |
| WO | 2014/110103 A1 | 7/2014 |
| WO | 2015089489 | 6/2015 |

OTHER PUBLICATIONS

Czeisler Charles A. et al: "Armodafinil for treatment of excessive sleepiness associated with shift work disorder: A randomized controlled study", Mayo Clinic Proceedings, vol. 84, No. 11, pp. 958-972, 2009.
Czeisler Charles A. et al: "Modafinil for excessive sleepiness associated with shift-work sleep disorder background" G.E.N. Oklahoma City (JRLS) N Engl J Med, pp. 476-486, 2005.
Mahmood et al., "Excessive daytime sleepiness", Handbook of Clinical Neurology, vol. 99 (3rd series) Sleep Disorders, Part 2, pp. 825-831, (2011).
Matheson, Jean K., "Disorders of Sleep", Office Practice of Neurology, 2nd Edition, Chapter 150, pp. 962-975, (2003).
Clinical Trail NCT03141086 publication date Jul. 22, 2019 available at http://clinicaltrials.gov.

* cited by examiner

*Primary Examiner* — Golam M Shameem
(74) *Attorney, Agent, or Firm* — Daniel Woods

(57) ABSTRACT

The invention relates to the use of a H3R inverse agonist for the treatment of shift work disorder.

12 Claims, 1 Drawing Sheet

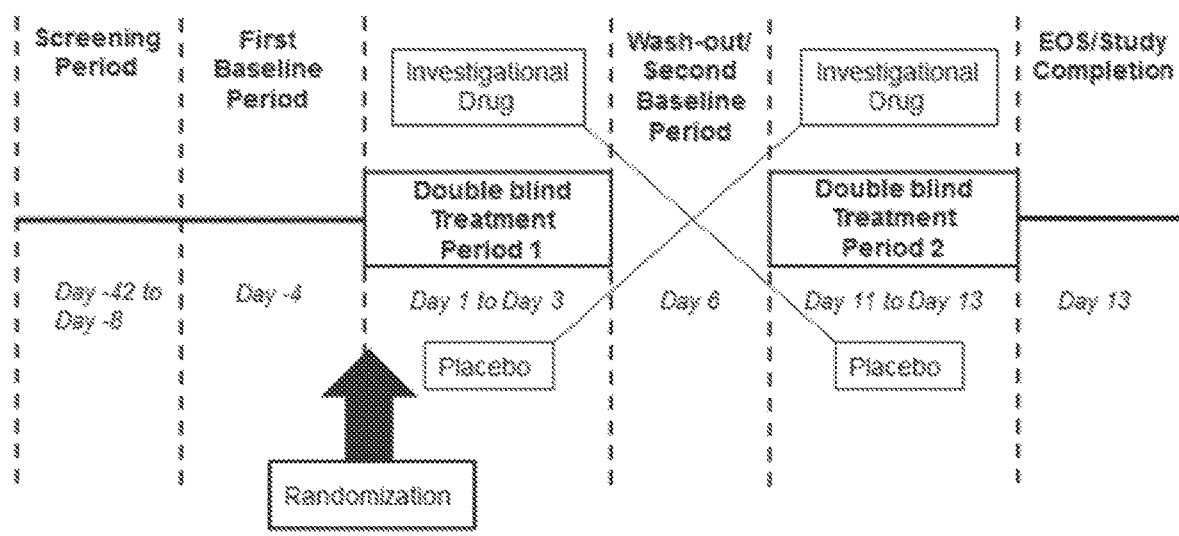

USE OF A H3R INVERSE AGONIST FOR THE TREATMENT OF SHIFT WORK DISORDER

FIELD OF THE INVENTION

The invention relates to the use of Compound (I), as defined herein, or pharmaceutically acceptable salt thereof, in the treatment of shift work disorder.

BACKGROUND OF THE INVENTION

In 2014, the American Academy of Sleep Medicine published the third edition of the International Classification of Sleep Disorders (ICSD-3), which is the most up-to-date classification of sleep disorders and provides diagnostic criteria. The ICSD-3 classified sleep disorders into six major categories (i.e. 1. insomnia, 2. sleep-related breathing disorders, 3. central disorders of hypersomnolence, 4. circadian rhythm sleep-wake disorders, 5. parasomnias and 6. sleep-related movement disorders).

As described in Neurotherapeutics (2012) 9:687-701, the major feature of circadian rhythm sleep-wake disorders is a persistent or recurrent misalignment between the individual's sleep pattern and that desired or regarded as societal norm. Regarding circadian rhythm sleep-wake disorders, the ICSD-3 included the following: 1. delayed sleep-wake phase disorder, 2. advanced sleep-wake phase disorder, 3. irregular sleep-wake rhythm disorder, 4. non-24 h sleep-wake rhythm disorder, 5. shift work disorder, 6. jet lag disorder and 7. circadian sleep-wake disorder not otherwise specified.

Shift work disorder (SWD) is a circadian rhythm sleep-wake disorder that results from the inability of some shift workers to adapt to the mismatch between the worker's sleep-wake imposed schedule (e.g. night-work schedule of sleep during the day and wake activities at night) and his/her internal circadian clock (i.e. endogenous circadian rhythm). Typically, SWD is characterized by (daytime) insomnia and/or excessive sleepiness (during work shift hours) that occur in relation to work hours scheduled during the usual time for sleep (at least in part). The four diagnostic criteria that need to be met for the diagnosis of SWD, according to the ICSD-3, are: 1) symptoms of excessive sleepiness with or without insomnia, accompanied by a reduction of total sleep time or fragmented sleep and associated with a shift work schedule (e.g. night shift work), 2) the symptoms have been present and associated with the shift work schedule for at least three months, 3) sleep log and actigraphy monitoring (whenever possible and preferably with concurrent light exposure measurement) for at least 14 days (work and free days) demonstrate a disturbed sleep and wake pattern, and 4) the sleep and/or wake disturbance are not better explained by another current sleep disorder, medical or neurological disorders, mental disorder, medication use, poor sleep hygiene or substance abuse disorder.

Shift work comprises work schedules that are outside the typical 9 am to 5 pm workday. Shifts go by different names depending on the work hours, thus shift work refers, for example, to "evening shift" (i.e. generally defined as work hours of from 2 pm to midnight), "night shift" (i.e. generally defined as work hours of from 9 pm to 8 am, such as of from 10 pm to 6 am), "early morning shift" (i.e. generally defined as work schedules starting at 4 am), "rotating shifts" (e.g. a rotating night shift consisting of several consecutive night shifts, for example four days, followed by several days off, such as two days, and repeat), "compressed work shift" (i.e. generally defined as work schedule with 12-hour shifts) and "irregular shift" (i.e. irregular work shift schedules). There is well-documented evidence (Schwartz and Roth 2006, Drake, et al 2004) showing the significant negative effect that shift work, in particular night shifts, have on health (e.g. increased risk of medical disorders, such as cardiovascular diseases, mood disorders, fatigue and peptic ulcer), productivity (e.g. impaired learning, cognition, creativity and work performance), and safety (e.g. increased risk of sleepiness-related accidents, impaired alertness). The prevalence of SWD is about 10-40% of the shift worker population and about 3% of the total population. There is an important medical need to be met for shift work disorder patients, in particular because of the additional health problems, decreased work performance, cognitive function impairment [e.g. as measured by the Symbol Digit Modalities Test (SDMT, Smith, 1968), Paced Auditory Serial Addition Test (PASAT, Rao, 1990) and computerized tests (e.g. Cho, et al 2011, Grove, et al 2014)], increased risk of accidents (e.g. at work and on the commute to and from work) and impaired quality of life, associated with SWD.

It has been shown that the quality of life in shift workers diagnosed with SWD compared to that of healthy shift workers is impaired, for example SF-8 physical and mental components scores were significantly lower in the former population (Asaoka et al, Chronobiology International, 30, 2013, 628). Currently available drugs used to modulate wakefulness and sleep, such as drugs that promote wakefulness, suffer from a number of shortcomings. Modafinil {i.e. 2-(benzhydrylsulfinyl)acetamide, or 2-[(diphenylmethyl)sulfinyl]acetamide} is a wake-promoting agent, whose structure is disclosed in U.S. Pat. No. 4,177,290, and which has been approved by the US Food and Drug Administration (FDA) for use in the treatment of narcolepsy and shift work disorder. The use of modafinil and armodafinil (i.e. R-modafinil) for the treatment of excessive sleepiness associated with SWD is disclosed in *N. Engl. J. Med.*, 2005, 353, 476-486 and in *Mayo Clin. Proc.*, 2009, 84 (11), 958-972, respectively. In addition, they are indicated to improve wakefulness in adult patients with excessive sleepiness associated with obstructive sleep apnea (OSA) and narcolepsy. However, in Europe, the European Medicines Agency (EMA) recommended the restriction of all modafinil's indications except for narcolepsy due to unfavorable risk/benefit profile; for example, it is associated with increased risk for development of skin or hypersensitivity reactions and neuropsychiatric disorders. In addition, particular cardiovascular risks have also been associated with modafinil (EMA 2010). Nevertheless, a modest but statistically significant improvement was observed in the mean sleep latency (MSLT) in SWD patients (*N. Engl. J. Med.*, 2005, 353, 476-486). However, the clinical relevance of this increase is questionable as, at the end of the study, many of the patients still showed evidence of excessive sleepiness during the night shift Accordingly, there is a need to identify new therapeutic agents that can be used to treat SWD, in particular drugs that are effective on sleepiness during the final hours of a work shift, in particular in night shifts. I It has been found that Compound (I) may be an ideal candidate in the treatment of SWD having therapeutic advantages, such as one or more of the following:

i) it reduces excessive sleepiness (i.e. improves wakefulness) during work shift hours, for example, it decreases excessive sleepiness during work shift hours during night shift (e.g. of from 10 pm to 8 am) compared to placebo;

ii) it reduces excessive sleepiness (i.e. improves wakefulness) during final hours of the night work shift (i.e. in early morning hours, such as of from 4 am to 8 am, in particular of from 6 am to 8 am), for example, it decreases excessive sleepiness during final hours of the night work shift (i.e. in early morning hours, such as of from 4 am to 8 am, in particular of from 6 am to 8 am) compared to placebo;

iii) it reduces excessive sleepiness (i.e. improves wakefulness) during final hours of the night work shift and the commute home from work (i.e. in early morning hours, such as of from 4 am to 8 am, in particular of from 6 am to 8 am), for example, it decreases excessive sleepiness during final hours of the night work shift and the commute home from work (i.e. in early morning hours, such as of from 4 am to 8 am, in particular of from 6 am to 8 am) compared to placebo;

iv) it increases sleep latency as measured by the multiple sleep latency test (MSLT) [Littner et al, *Sleep*, 2005, 28 (10), 113-121] or performed in other studies in shift work disorder patients: *N. Engl. J. Med.*, 2005, 353, 476-486 and in *Mayo Clin. Proc.*, 2009, 84 (11), 958-972] compared to placebo (e.g. at least 1 minute difference in MSLT sleep latency compared to placebo);

v) it improves clinical impression of sleepiness, for example, as assessed from Clinical Global Impression scale (CGI; Guy 1976) score of overall sleepiness compared to placebo;

vi) it improves subjective sleepiness, for example, it improves Karolinska sleepiness scale (KSS, Akerstedt and Gillberg 1990) score compared to placebo;

vii) it reduces excessive sleepiness (i.e. improves wakefulness during work shift hours, e.g. during night shift) without affecting sleep [e.g. as measured by sleep diary data or polysomnography (PSG) measurements (Berry et al 2016)];

viii) it reduces excessive sleepiness without affecting daytime sleep (e.g. without causing insomnia); for example, it decreases excessive sleepiness (during work shift hours, e.g. during the night shift) without affecting (daytime) sleep (e.g. without causing insomnia) compared to placebo;

ix) it improves cognitive function, for example, it improves one or more of the cognitive domains selected from the group consisting of learning, psychomotor function, attention, sustained attention, working memory, episodic memory, executive function, auditory information processing speed, auditory information processing flexibility, and calculation ability, [e.g. as measured by the Symbol Digit Modalities Test (SDMT, Smith, 1968), Paced Auditory Serial Addition Test (PASAT, Rao, 1990) and computerized tests (e.g. Cho, et al 2011, Grove, et al 2014)], compared to placebo; or x) it has a favorable safety profile, such as a favorable profile in relation to skin reactions, psychiatric adverse events or cardiovascular adverse events (e.g. blood pressure, heart rate, electrocardiography parameters); for example, it has a better safety profile compared to known therapeutic agent/s (e.g. modafinil or armodafinil).

SUMMARY OF THE INVENTION

The invention relates to Compound (I), or pharmaceutically acceptable salt thereof, for:
use in the treatment of shift work disorder;
use as an agent modulating circadian rhythm dysfunctions due to shift work;
use in the treatment of excessive sleepiness associated with shift work disorder;
use in promoting wakefulness in a shift work disorder patient;
use in the treatment of excessive sleepiness in a shift work disorder patient; or
use in the treatment of cognitive function impairment associated with shift work disorder; such as learning impairment, psychomotor function impairment, attention impairment, sustained attention impairment, working memory impairment, episodic memory impairment, executive function impairment, auditory information processing speed impairment, auditory information processing flexibility impairment, and calculation ability impairment, which are each associated with shift work disorder.

In another aspect, the invention relates to a pharmaceutical composition comprising Compound (I), or pharmaceutically acceptable salt thereof, and at least one pharmaceutically acceptable excipient, for:
use in the treatment of shift work disorder;
use as an agent modulating circadian rhythm dysfunctions due to shift work;
use in the treatment of excessive sleepiness associated with shift work disorder;
use in promoting wakefulness in a shift work disorder patient;
use in the treatment of excessive sleepiness in a shift work disorder patient; or
use in the treatment of cognitive function impairment associated with shift work disorder; such as learning impairment, psychomotor function impairment, attention impairment, sustained attention impairment, working memory impairment, episodic memory impairment, executive function impairment, auditory information processing speed impairment, auditory information processing flexibility impairment, and calculation ability impairment, which are each associated with shift work disorder.

In yet another aspect, the invention relates to a pharmaceutical combination comprising Compound (I), or pharmaceutically acceptable salt thereof, and at least one further pharmaceutical active ingredient, for:
use in the treatment of shift work disorder;
use as an agent modulating circadian rhythm dysfunctions due to shift work;
use in the treatment of excessive sleepiness associated with shift work disorder;
use in promoting wakefulness in a shift work disorder patient;
use in the treatment of excessive sleepiness in a shift work disorder patient; or
use in the treatment of cognitive function impairment associated with shift work disorder; such as learning impairment, psychomotor function impairment, attention impairment, sustained attention impairment, working memory impairment, episodic memory impairment, executive function impairment, auditory information processing speed impairment, auditory information processing flexibility impairment, and calculation ability impairment, which are each associated with shift work disorder.

Further pharmaceutical active ingredients to be combined with Compound (I), or pharmaceutically acceptable salt thereof, for use according to the invention, are, for example, wakefulness-promoting agents, such as modafinil, armodafinil, caffeine, methylphenidate, dextroamphetamine and sodium oxybate; in particular, modafinil or armodafinil.

BRIEF DESCRIPTION OF THE DRAWINGS

FIG. 1. Flowchart describing a randomized, double-blind, placebo controlled, crossover Proof of Concept study to investigate the safety and efficacy of Compound 1 as compared with placebo.

DETAILED DESCRIPTION OF THE INVENTION

Embodiments of the Present Invention are:

Embodiments (a)

Embodiment 1a: Compound (I), or pharmaceutically acceptable salt thereof, for use in the treatment of shift work disorder.

Embodiment 2a: Compound (I), or pharmaceutically acceptable salt thereof, for use as an agent modulating circadian rhythm dysfunctions due to shift work.

Embodiment 3a: Compound (I), or pharmaceutically acceptable salt thereof, for use in the treatment of excessive sleepiness associated with shift work disorder.

Embodiment 4a: Compound (I), or pharmaceutically acceptable salt thereof, for use in promoting wakefulness in a shift work disorder patient.

Embodiment 5a: Compound (I), or pharmaceutically acceptable salt thereof, for use in the treatment of excessive sleepiness in a shift work disorder patient.

Embodiment 6a: Compound (I), or pharmaceutically acceptable salt thereof, for use in the treatment of cognitive function impairment associated with shift work disorder, in particular wherein cognitive function comprises cognitive domains selected from the group consisting of learning, psychomotor function, attention, sustained attention, working memory, episodic memory, executive function, auditory information processing speed, auditory information processing flexibility, and calculation ability; in a particular embodiment, wherein it comprises one or more cognitive domains selected from attention, sustained attention and psychomotor function; in another particular embodiment, wherein it comprises one or more cognitive domains selected from episodic memory, working memory and executive function.

Embodiment 7a: Compound (I), or pharmaceutically acceptable salt thereof, for use according to any one of embodiments 1a to 6a, wherein Compound (I), or pharmaceutically acceptable salt thereof, is administered in combination with one or more further pharmaceutical active ingredient.

Embodiment 8a: Compound (I), or pharmaceutically acceptable salt thereof, for use according to embodiment 7a, wherein the further pharmaceutical active ingredient is a wakefulness-promoting agent.

Embodiment 9a: Compound (I), or pharmaceutically acceptable salt thereof, for use according to embodiment 8a, wherein the wakefulness-promoting agent is selected from the group consisting of modafinil, armodafinil, caffeine, methylphenidate, dextroamphetamine and sodium oxybate, or pharmaceutically acceptable salts thereof.

Embodiment 10a: Compound (I), or pharmaceutically acceptable salt thereof, for use according to embodiment 8a, wherein the wakefulness-promoting agent is modafinil or armodafinil, or pharmaceutically acceptable salts thereof.

Embodiment 11a: Compound (I), or pharmaceutically acceptable salt thereof, for use according to any one of embodiments 1a to 10a, wherein Compound (I), is administered in an amount of from 0.1 mg/day to 100 mg/day, in particular of from 1 mg/day to 50 mg/day, such as of from 2 mg/day to 10 mg/day, more particularly 5 mg/day.

Embodiment 12a: Compound (I), or pharmaceutically acceptable salt thereof, for use according to any one of embodiments 1a to 11a, wherein Compound (I), or pharmaceutically acceptable salt thereof, is administered to a sleepy insomniac shift work disorder patient or a sleepy non-insomniac shift work disorder patient.

Embodiment 13a: Compound (I), or pharmaceutically acceptable salt thereof, for use according to any one of embodiments 1a to 12a, wherein Compound (I), or pharmaceutically acceptable salt thereof, is administered orally.

Embodiment 14a: Compound (I), or pharmaceutically acceptable salt thereof, for use according to any one of the preceding embodiments, wherein shift work disorder is associated with night shift work, rotating shift work, evening shift work or early morning shift work, in particular, night shift work, such as permanent night shift work or rotating night shift work.

Embodiment 15a: Compound (I), or pharmaceutically acceptable salt thereof, for use according to any one of the preceding embodiments, wherein shift work is night shift work, rotating shift work, evening shift work or early morning shift work, in particular, night shift work, such as permanent night shift work or rotating night shift work.

Embodiment 16a: A combination comprising Compound (I), or pharmaceutically acceptable salt thereof, and at least one active ingredient selected from the group consisting of modafinil, armodafinil, caffeine, methylphenidate, dextroamphetamine and sodium oxybate, or pharmaceutically acceptable salts thereof.

Embodiments (b)

Embodiment 1b: A pharmaceutical composition comprising Compound (I), or pharmaceutically acceptable salt thereof, and at least one pharmaceutically acceptable excipient, for use in the treatment of shift work disorder.

Embodiment 2b: A pharmaceutical composition comprising Compound (I), or pharmaceutically acceptable salt thereof, and at least one pharmaceutically acceptable excipient, for use as an agent modulating circadian rhythm dysfunctions due to shift work.

Embodiment 3b: A pharmaceutical composition comprising Compound (I), or pharmaceutically acceptable salt thereof, and at least one pharmaceutically acceptable excipient, for use in the treatment of excessive sleepiness associated with shift work disorder.

Embodiment 4b: A pharmaceutical composition comprising Compound (I), or pharmaceutically acceptable salt thereof, and at least one pharmaceutically acceptable excipient, for use in promoting wakefulness in a shift work disorder patient.

Embodiment 5b: A pharmaceutical composition comprising Compound (I), or pharmaceutically acceptable salt thereof, and at least one pharmaceutically acceptable excipient, for use in the treatment of excessive sleepiness in a shift work disorder patient.

Embodiment 6b: A pharmaceutical composition comprising Compound (I), or pharmaceutically acceptable salt thereof, and at least one pharmaceutically acceptable excipient, for use in the treatment of cognitive function impairment associated with shift work disorder, in particular wherein cognitive function comprises cognitive domains selected from the group consisting of learning, psychomotor function, attention, sustained attention, working memory, episodic memory, executive function, auditory information processing speed, auditory information processing flexibility, and calculation ability; in a particular embodiment, wherein it comprises one or more cognitive domains selected from attention, sustained attention and psychomotor function; in another particular embodiment, wherein it comprises one or more cognitive domains selected from episodic memory, working memory and executive function.

Embodiment 7b: A pharmaceutical composition comprising Compound (I), or pharmaceutically acceptable salt thereof, and at least one pharmaceutically acceptable excipient, for use according to any one of embodiments 1b to 6b, wherein Compound (I), or pharmaceutically acceptable salt thereof, is administered in combination with one or more further pharmaceutical active ingredient.

Embodiment 8b: A pharmaceutical composition comprising Compound (I), or pharmaceutically acceptable salt thereof, and at least one pharmaceutically acceptable excipient, for use according to embodiment 7b, wherein the further pharmaceutical active ingredient is a wakefulness-promoting agent.

Embodiment 9b: A pharmaceutical composition comprising Compound (I), or pharmaceutically acceptable salt thereof, and at least one pharmaceutically acceptable excipient, for use according to embodiment 8b, wherein the wakefulness-promoting agent is selected from the group consisting of modafinil, armodafinil, caffeine, methylphenidate, dextroamphetamine and sodium, oxybate, or pharmaceutically acceptable salts thereof.

Embodiment 10b: A pharmaceutical composition comprising Compound (I), or pharmaceutically acceptable salt thereof, and at least one pharmaceutically acceptable excipient, for use according to embodiment 8b, wherein the wakefulness-promoting agent is modafinil or armodafinil, or pharmaceutically acceptable salts thereof.

Embodiment 11b: A pharmaceutical composition comprising Compound (I), or pharmaceutically acceptable salt thereof, and at least one pharmaceutically acceptable excipient, for use according to any one of embodiments 1b to 10b, wherein Compound (I) is administered in an amount of from 0.1 mg/day to 100 mg/day, in particular of from 1 mg/day to 50 mg/day, such as of from 2 mg/day to 10 mg/day, more particularly 5 mg/day.

Embodiment 12b: A pharmaceutical composition comprising Compound (I), or pharmaceutically acceptable salt thereof, and at least one pharmaceutically acceptable excipient, for use according to any one of embodiments 1b to 11b, wherein Compound (I), or pharmaceutically acceptable salt thereof, is administered to a sleepy insomniac shift work disorder patient or a sleepy non-insomniac shift work disorder patient.

Embodiment 13b: A pharmaceutical composition comprising Compound (I), or pharmaceutically acceptable salt thereof, and at least one pharmaceutically acceptable excipient, for use according to any one of embodiments 1b to 12b, wherein Compound (I), or pharmaceutically acceptable salt thereof, is administered orally.

Embodiment 14b: A pharmaceutical composition comprising Compound (I), or pharmaceutically acceptable salt thereof, and at least one pharmaceutically acceptable excipient, for use according to any one of the preceding embodiments, wherein shift work disorder is associated with night shift work, rotating shift work, evening shift work or early morning shift work, in particular, night shift work, such as permanent night shift work or rotating night shift work.

Embodiment 15b: A pharmaceutical composition comprising Compound (I), or pharmaceutically acceptable salt thereof, and at least one pharmaceutically acceptable excipient, for use according to any one of the preceding embodiments, wherein shift work is night shift work, rotating shift work, evening shift work or early morning shift work, in particular, night shift work, such as permanent night shift work or rotating night shift work.

Embodiments (c)

Embodiment 1c: A pharmaceutical combination comprising Compound (I), or pharmaceutically acceptable salt thereof, and at least one further pharmaceutical active ingredient, for use in the treatment of shift work disorder.

Embodiment 2c: A pharmaceutical combination comprising Compound (I), or pharmaceutically acceptable salt thereof, and at least one further pharmaceutical active ingredient, for use as an agent modulating circadian rhythm dysfunctions due to shift work.

Embodiment 3c: A pharmaceutical combination comprising Compound (I), or pharmaceutically acceptable salt thereof, and at least one further pharmaceutical active ingredient, for use in the treatment of excessive sleepiness associated with shift work disorder.

Embodiment 4c: A pharmaceutical combination comprising Compound (I), or pharmaceutically acceptable salt thereof, and at least one further pharmaceutical active ingredient, for use in promoting wakefulness in a shift work disorder patient.

Embodiment 5c: A pharmaceutical combination comprising Compound (I), or pharmaceutically acceptable salt thereof, and at least one further pharmaceutical active ingredient, for use in the treatment of excessive sleepiness in a shift work disorder patient.

Embodiment 6c: A pharmaceutical combination comprising Compound (I), or pharmaceutically acceptable salt thereof, and at least one further pharmaceutical active ingredient, for use in the treatment of cognitive function impairment associated with shift work disorder, in particular wherein cognitive function comprises cognitive domains selected from the group consisting of learning, psychomotor function, attention, sustained attention, working memory, episodic memory, executive function, auditory information processing speed, auditory information processing flexibility, and calculation ability; in a particular embodiment, wherein it comprises one or more cognitive domains selected from attention, sustained attention and psychomotor function; in another particular embodiment, wherein it comprises one or more cognitive domains selected from episodic memory, working memory and executive function.

Embodiment 7c: A pharmaceutical combination comprising Compound (I), or pharmaceutically acceptable salt thereof, and at least one further pharmaceutical active ingredient, for use according to any one of embodiments 1c to 6c, wherein the further pharmaceutical active ingredient is a wakefulness-promoting agent.

Embodiment 8c: A pharmaceutical combination comprising Compound (I), or pharmaceutically acceptable salt thereof, and at least one further pharmaceutical active ingredient, for use according to embodiment 7c, wherein the wakefulness-promoting agent is selected from the group consisting of modafinil, armodafinil, caffeine, methylphenidate, dextroamphetamine and sodium oxybate, or pharmaceutically acceptable salts thereof.

Embodiment 9c: A pharmaceutical combination comprising Compound (I), or pharmaceutically acceptable salt thereof, and at least one further pharmaceutical active ingredient, for use according to embodiment 7c, wherein the wakefulness-promoting agent is modafinil or armodafinil, or pharmaceutically acceptable salts thereof.

Embodiment 10c: A pharmaceutical combination comprising Compound (I), or pharmaceutically acceptable salt thereof, and at least one further pharmaceutical active ingredient, for use according to any one of embodiments 1c to 9c, wherein Compound (I) is administered in an amount of from 0.1 mg/day to 100 mg/day, in particular of from 1 mg/day to 50 mg/day, such as of from 2 mg/day to 10 mg/day, more particularly 5 mg/day.

Embodiment 11c: A pharmaceutical combination comprising Compound (I), or pharmaceutically acceptable salt thereof, and at least one further pharmaceutical active ingredient, for use according to any one of embodiments 1c to 10c, wherein Compound (I), or pharmaceutically acceptable salt thereof, is administered to a sleepy insomniac shift work disorder patient or a sleepy non-insomniac shift work disorder patient.

Embodiment 12c: A pharmaceutical combination comprising Compound (I), or pharmaceutically acceptable salt thereof, and at least one further pharmaceutical active ingredient, for use according to any one of embodiments 1c to 11c, wherein Compound (I), or pharmaceutically acceptable salt thereof, is administered orally.

Embodiment 13c: A pharmaceutical combination comprising Compound (I), or pharmaceutically acceptable salt thereof, and at least one further pharmaceutical active ingredient, for use according to any one of the preceding embodiments, wherein shift work disorder is associated with night shift work, rotating shift work, evening shift work or early morning shift work, in particular, night shift work, such as permanent night shift work or rotating night shift work.

Embodiment 14c: A pharmaceutical combination comprising Compound (I), or pharmaceutically acceptable salt thereof, and at least one further pharmaceutical active ingredient, for use according to any one of the preceding embodiments, wherein shift work is night shift work, rotating shift work, evening shift work or early morning shift work, in particular, night shift work, such as permanent night shift work or rotating night shift work.

Embodiments (d)

Embodiment 1d: A method for treating shift work disorder, in a subject, in need thereof, comprising administering to said subject an effective amount of Compound (I), or pharmaceutically acceptable salt thereof.

Embodiment 2d: A method for modulating circadian rhythm dysfunctions due to shift work, in a subject, in need thereof, comprising administering to said subject an effective amount of Compound (I), or pharmaceutically acceptable salt thereof.

Embodiment 3d: A method for treating excessive sleepiness associated with shift work disorder in a subject, in need thereof, comprising administering to said subject an effective amount of Compound (I), or pharmaceutically acceptable salt thereof.

Embodiment 4d: A method for promoting wakefulness in a shift work disorder patient, in need thereof, comprising administering to said shift work disorder patient an effective amount of Compound (I), or pharmaceutically acceptable salt thereof.

Embodiment 5d: A method for treating excessive sleepiness in a shift work disorder patient, in need thereof, comprising administering to said shift work disorder patient an effective amount of Compound (I), or pharmaceutically acceptable salt thereof.

Embodiment 6d: A method for treating cognitive function impairment associated with shift work disorder, in a subject, in need thereof, comprising administering to said subject an effective amount of Compound (I), or pharmaceutically acceptable salt thereof, in particular wherein cognitive function comprises cognitive domains selected from the group consisting of learning, psychomotor function, attention, sustained attention, working memory, episodic memory, executive function, auditory information processing speed, auditory information processing flexibility, and calculation ability; in a particular embodiment, wherein it comprises one or more cognitive domains selected from attention, sustained attention and psychomotor function; in another particular embodiment, wherein it comprises one or more cognitive domains selected from episodic memory, working memory and executive function.

Embodiment 7d: A method according to any one of embodiments 1d to 6d, wherein Compound (I), or pharmaceutically acceptable salt thereof, is administered in combination with one or more further pharmaceutical active ingredient.

Embodiment 8d: A method according to embodiment 7d, wherein the further pharmaceutical active ingredient is a wakefulness-promoting agent.

Embodiment 9d: A method according to embodiment 8d, wherein the wakefulness-promoting agent is selected from the group consisting of modafinil, armodafinil, caffeine, methylphenidate, dextroamphetamine and sodium oxybate, or pharmaceutically acceptable salts thereof.

Embodiment 10d: A method according to embodiment 8d, wherein the wakefulness-promoting agent is modafinil or armodafinil, or pharmaceutically acceptable salt thereof.

Embodiment 11d: A method according to any one of embodiments 1d to 10d, wherein Compound (I) is administered in an amount of from 0.1 mg/day to 100 mg/day, in particular of from 1 mg/day to 50 mg/day, such as of from 2 mg/day to 10 mg/day, more particularly 5 mg/day.

Embodiment 12d: A method according to any one of embodiments 1d to 11d, wherein the subject or shift work disorder patient is a sleepy insomniac shift work disorder patient or a sleepy non-insomniac shift work disorder patient.

Embodiment 13d: A method according to any one of embodiments 1d to 12d, wherein Compound (I), or pharmaceutically acceptable salt thereof, is administered orally.

Embodiment 14d: A method according to any one of the preceding embodiments, wherein shift work disorder is associated with night shift work, rotating shift work, evening shift work or early morning shift work, in particular, night shift work, such as permanent night shift work or rotating night shift work.

Embodiment 15d: A method according to any one of the preceding embodiments, wherein shift work is night shift work, rotating shift work, evening shift work or early morning shift work, in particular, night shift work, such as permanent night shift work or rotating night shift work.

Embodiments (e)

Embodiment 1e: A method for treating shift work disorder, in a subject, in need thereof, comprising administering to said subject a pharmaceutical composition comprising an effective amount of Compound (I), or pharmaceutically acceptable salt thereof, and at least one pharmaceutically acceptable excipient.

Embodiment 2e: A method for modulating circadian rhythm dysfunctions due to shift work, in a subject, in need thereof, comprising administering to said subject a pharmaceutical composition comprising an effective amount of Compound (I), or pharmaceutically acceptable salt thereof, and at least one pharmaceutically acceptable excipient.

Embodiment 3e: A method for treating excessive sleepiness associated with shift work disorder, in a subject, in need thereof, comprising administering to said subject a pharmaceutical composition comprising an effective amount of Compound (I), or pharmaceutically acceptable salt thereof, and at least one pharmaceutically acceptable excipient.

Embodiment 4e: A method for promoting wakefulness in a shift work disorder patient, in need thereof, comprising administering to said shift work disorder patient a pharmaceutical composition comprising an effective amount of Compound (I), or pharmaceutically acceptable salt thereof, and at least one pharmaceutically acceptable excipient.

Embodiment 5e: A method for treating excessive sleepiness in a shift work disorder patient, in need thereof, comprising administering to said shift work disorder patient a pharmaceutical composition comprising an effective amount of Compound (I), or pharmaceutically acceptable salt thereof, and at least one pharmaceutically acceptable excipient.

Embodiment 6e: A method for treating cognitive function impairment associated with shift work disorder, in a subject, in need thereof, comprising administering to said subject a pharmaceutical composition comprising an effective amount of Compound (I), or pharmaceutically acceptable salt thereof, and at least one pharmaceutically acceptable excipient, in particular wherein cognitive function comprises cognitive domains selected from the group consisting of learning, psychomotor function, attention, sustained attention, working memory, episodic memory, executive function, auditory information processing speed, auditory information processing flexibility, and calculation ability; in a particular embodiment, wherein it comprises one or more cognitive domains selected from attention, sustained attention and psychomotor function; in another particular embodiment, wherein it comprises one or more cognitive domains selected from episodic memory, working memory and executive function.

Embodiment 7e: A method according to any one of embodiments 1e to 6e, wherein Compound (I), or pharmaceutically acceptable salt thereof, is administered in combination with one or more further pharmaceutical active ingredient.

Embodiment 8e: A method according to embodiment 7e, wherein the further pharmaceutical active ingredient is a wakefulness-promoting agent.

Embodiment 9e: A method according to embodiment 8e, wherein the wakefulness-promoting agent is selected from the group consisting of modafinil, armodafinil, caffeine, methylphenidate, dextroamphetamine and sodium oxybate, or pharmaceutically acceptable salts thereof.

Embodiment 10e: A method according to embodiment 8e, wherein the wakefulness-promoting agent is modafinil or armodafinil, or pharmaceutically acceptable salt thereof.

Embodiment 11e: A method according to any one of embodiments 1e to 10e, wherein Compound (I) is administered in an amount of from 0.1 mg/day to 100 mg/day, in particular of from 1 mg/day to 50 mg/day, such as of from 2 mg/day to 10 mg/day, more particularly 5 mg/day.

Embodiment 12e: A method according to any one of embodiments 1e to 11e, wherein the subject or shift work disorder patient is a sleepy insomniac shift work disorder patient or a sleepy non-insomniac shift work disorder patient.

Embodiment 13e: A method according to any one of embodiments 1e to 12e, wherein Compound (I), or pharmaceutically acceptable salt thereof, is administered orally.

Embodiment 14e: A method according to any one of the preceding embodiments, wherein shift work disorder is associated with night shift work, rotating shift work, evening shift work or early morning shift work, in particular, night shift work, such as permanent night shift work or rotating night shift work.

Embodiment 15e: A method according to any one of the preceding embodiments, wherein shift work is night shift work, rotating shift work, evening shift work or early morning shift work, in particular, night shift work, such as permanent night shift work or rotating night shift work.

Embodiments (f)

Embodiment 1f: A method for treating shift work disorder, in a subject, in need thereof, comprising administering to said subject a pharmaceutical combination comprising an effective amount of Compound (I), or pharmaceutically acceptable salt thereof, and at least one further pharmaceutical active ingredient.

Embodiment 2f: A method for modulating circadian rhythm dysfunctions due to shift work, in a subject, in need thereof, comprising administering to said subject a pharmaceutical combination comprising an effective amount of Compound (I), or pharmaceutically acceptable salt thereof, and at least one further pharmaceutical active ingredient.

Embodiment 3f: A method for treating excessive sleepiness associated with shift work disorder, in a subject, in need thereof, comprising administering to said subject a pharmaceutical combination comprising an effective amount of Compound (I), or pharmaceutically acceptable salt thereof, and at least one further pharmaceutical active ingredient.

Embodiment 4f: A method for promoting wakefulness in a shift work disorder patient, in need thereof, comprising administering to said shift work disorder patient a pharmaceutical combination comprising an effective amount of Compound (I), or pharmaceutically acceptable salt thereof, and at least one further pharmaceutical active ingredient.

Embodiment 5f: A method for treating excessive sleepiness in a shift work disorder patient, in need thereof, comprising administering to said shift work disorder patient a pharmaceutical combination comprising an effective amount of Compound (I), or pharmaceutically acceptable salt thereof, and at least one further pharmaceutical active ingredient.

Embodiment 6f: A method for treating cognitive function impairment associated with shift work disorder, in a subject, in need thereof, comprising administering to said subject a pharmaceutical combination comprising an effective amount of Compound (I), or pharmaceutically acceptable salt thereof, and at least one further pharmaceutical active ingredient, in particular wherein cognitive function comprises cognitive domains selected from the group consisting of learning, psychomotor function, attention, sustained attention, working memory, episodic memory, executive function, auditory information processing speed, auditory information processing flexibility, and calculation ability; in a particular embodiment, wherein it comprises one or more cognitive domains selected from attention, sustained attention and psychomotor function; in another particular embodiment, wherein it comprises one or more cognitive domains selected from episodic memory, working memory and executive function.

Embodiment 7f: A method according to embodiment 6f, wherein the further pharmaceutical active ingredient is a wakefulness-promoting agent.

Embodiment 8f: A method according to embodiment 7f, wherein the wakefulness-promoting agent is selected from the group consisting of modafinil, armodafinil, caffeine, methylphenidate, dextroamphetamine and sodium oxybate, or pharmaceutically acceptable salts thereof.

Embodiment 9f: A method according to embodiment 7f, wherein the wakefulness-promoting agent is modafinil or armodafinil, or pharmaceutically acceptable salt thereof.

Embodiment 10f: A method according to any one of embodiments 1f to 9f, wherein Compound (I) is administered in an amount of from 0.1 mg/day to 100 mg/day, in particular of from 1 mg/day to 50 mg/day, such as of from 2 mg/day to 10 mg/day, more particularly 5 mg/day.

Embodiment 11f: A method according to any one of embodiments 1f to 10f, wherein the subject or shift work disorder patient is a sleepy insomniac shift work disorder patient or a sleepy non-insomniac shift work disorder patient.

Embodiment 12f: A method according to any one of embodiments 1f to 11f, wherein Compound (I), or pharmaceutically acceptable salt thereof, is administered orally.

Embodiment 13f: A method according to any one of the preceding embodiments, wherein shift work disorder is associated with night shift work, rotating shift work, evening shift work or early morning shift work, in particular, night shift work, such as permanent night shift work or rotating night shift work.

Embodiment 14f: A method according to any one of the preceding embodiments, wherein shift work is night shift work, rotating shift work, evening shift work or early morning shift work, in particular, night shift work, such as permanent night shift work or rotating night shift work.

Embodiments (q)

Embodiment 1g: Use of Compound (I), or pharmaceutically acceptable salt thereof, for the manufacture of a medicament for the treatment of shift work disorder.

Embodiment 2g: Use of Compound (I), or pharmaceutically acceptable salt thereof, for the manufacture of a medicament being an agent modulating circadian rhythm dysfunctions due to shift work.

Embodiment 3g: Use of Compound (I), or pharmaceutically acceptable salt thereof, for the manufacture of a medicament for the treatment of excessive sleepiness associated with shift work disorder.

Embodiment 4g: Use of Compound (I), or pharmaceutically acceptable salt thereof, for the manufacture of a medicament for promoting wakefulness in a shift work disorder patient.

Embodiment 5g: Use of Compound (I), or pharmaceutically acceptable salt thereof, for the manufacture of a medicament for the treatment of excessive sleepiness in a shift work disorder patient.

Embodiment 6g: Use of Compound (I), or pharmaceutically acceptable salt thereof, for the manufacture of a medicament for the treatment of cognitive function impairment associated with shift work disorder, in particular wherein cognitive function comprises cognitive domains selected from the group consisting of learning, psychomotor function, attention, sustained attention, working memory, episodic memory, executive function, auditory information processing speed, auditory information processing flexibility, and calculation ability; in a particular embodiment, wherein it comprises one or more cognitive domains selected from attention, sustained attention and psychomotor function; in another particular embodiment, wherein it comprises one or more cognitive domains selected from episodic memory, working memory and executive function.

Embodiment 7g: Use of Compound (I), or pharmaceutically acceptable salt thereof, for the manufacture of a medicament according to any one of embodiments 1g to 6g, wherein Compound (I), or pharmaceutically acceptable salt thereof, is administered in combination with one or more further pharmaceutical active ingredient.

Embodiment 8g: Use of Compound (I), or pharmaceutically acceptable salt thereof, for the manufacture of a medicament according to embodiment 7g, wherein the further pharmaceutical active ingredient is a wakefulness-promoting agent.

Embodiment 9g: Use of Compound (I), or pharmaceutically acceptable salt thereof, for the manufacture of a medicament according to embodiment 8g, wherein the wakefulness-promoting agent is selected from the group consisting of modafinil, armodafinil, caffeine, methylphenidate, dextroamphetamine and sodium oxybate, or pharmaceutically acceptable salts thereof.

Embodiment 10g: Use of Compound (I), or pharmaceutically acceptable salt thereof, for the manufacture of a medicament according to embodiment 8g, wherein the wakefulness-promoting agent is modafinil or armodafinil, or pharmaceutically acceptable salts thereof.

Embodiment 11g: Use of Compound (I), or pharmaceutically acceptable salt thereof, for the manufacture of a medicament according to any one of embodiments 1g to 10g, wherein Compound (I) is administered in an amount of from 0.1 mg/day to 100 mg/day, in particular of from 1 mg/day to 50 mg/day, such as of from 2 mg/day to 10 mg/day, more particularly 5 mg/day.

Embodiment 12g: Use of Compound (I), or pharmaceutically acceptable salt thereof, for the manufacture of a medicament according to any one of embodiments 1g to 11g, wherein Compound (I), or pharmaceutically acceptable salt thereof, is administered to a sleepy insomniac shift work disorder patient or a sleepy non-insomniac shift work disorder patient.

Embodiment 13g: Use of Compound (I), or pharmaceutically acceptable salt thereof, for the manufacture of a medicament according to any one of embodiments 1g to 12g, wherein Compound (I), or pharmaceutically acceptable salt thereof, is administered orally.

Embodiment 14g: Use of Compound (I), or pharmaceutically acceptable salt thereof, for the manufacture of a medicament according to any one of the preceding embodiments, wherein shift work disorder is associated with night shift work, rotating shift work, evening shift work or early morning shift work, in particular, night shift work, such as permanent night shift work or rotating night shift work.

Embodiment 15g: Use of Compound (I), or pharmaceutically acceptable salt thereof, for the manufacture of a medicament according to any one of the preceding embodiments, wherein shift work is night shift work, rotating shift work, evening shift work or early morning shift work, in particular, night shift work, such as permanent night shift work or rotating night shift work.

Embodiments (h)

Embodiment 1h: Use of a pharmaceutical composition comprising Compound (I), or pharmaceutically acceptable salt thereof, and at least one pharmaceutically acceptable excipient, for the manufacture of a medicament for the treatment of shift work disorder.

Embodiment 2h: Use of a pharmaceutical composition comprising Compound (I), or pharmaceutically acceptable salt thereof, and at least one pharmaceutically acceptable excipient, for the manufacture of a medicament being an agent modulating circadian rhythm dysfunctions due to shift work.

Embodiment 3h: Use of a pharmaceutical composition comprising Compound (I), or pharmaceutically acceptable salt thereof, and at least one pharmaceutically acceptable excipient, for the manufacture of a medicament for the treatment of excessive sleepiness associated with shift work disorder.

Embodiment 4h: Use of a pharmaceutical composition comprising Compound (I), or pharmaceutically acceptable salt thereof, and at least one pharmaceutically acceptable excipient, for the manufacture of a medicament for promoting wakefulness in a shift work disorder patient.

Embodiment 5h: Use of a pharmaceutical composition comprising Compound (I), or pharmaceutically acceptable salt thereof, and at least one pharmaceutically acceptable excipient, for the manufacture of a medicament for the treatment of excessive sleepiness in a shift work disorder patient.

Embodiment 6h: Use of a pharmaceutical composition comprising Compound (I), or pharmaceutically acceptable salt thereof, and at least one pharmaceutically acceptable excipient, for the manufacture of a medicament for the treatment of cognitive function impairment associated with shift work disorder, in particular wherein cognitive function comprises cognitive domains selected from the group consisting of learning, psychomotor function, attention, sustained attention, working memory, episodic memory, executive function, auditory information processing speed, auditory information processing flexibility, and calculation ability; in a particular embodiment, wherein it comprises one or more cognitive domains selected from attention, sustained attention and psychomotor function; in another particular embodiment, wherein it comprises one or more cognitive domains selected from episodic memory, working memory and executive function.

Embodiment 7h: Use of a pharmaceutical composition comprising Compound (I), or pharmaceutically acceptable salt thereof, and at least one pharmaceutically acceptable excipient, for the manufacture of a medicament according to any one of embodiments 1h to 6h, wherein Compound (I), or pharmaceutically acceptable salt thereof, is administered in combination with one or more further pharmaceutical active ingredient.

Embodiment 8h: Use of a pharmaceutical composition comprising Compound (I), or pharmaceutically acceptable salt thereof, and at least one pharmaceutically acceptable excipient, for the manufacture of a medicament according to embodiment 7h, wherein the further pharmaceutical active ingredient is a wakefulness-promoting agent.

Embodiment 9h: Use of a pharmaceutical composition comprising Compound (I), or pharmaceutically acceptable salt thereof, and at least one pharmaceutically acceptable excipient, for the manufacture of a medicament according to embodiment 8h, wherein the wakefulness-promoting agent is selected from the group consisting of modafinil, armodafinil, caffeine, methylphenidate, dextroamphetamine and sodium, oxybate, or pharmaceutically acceptable salts thereof.

Embodiment 10h: Use of a pharmaceutical composition comprising Compound (I), or pharmaceutically acceptable salt thereof, and at least one pharmaceutically acceptable excipient, for the manufacture of a medicament according to embodiment 8h, wherein the wakefulness-promoting agent is modafinil or armodafinil, or pharmaceutically acceptable salts thereof.

Embodiment 11h: Use of a pharmaceutical composition comprising Compound (I), or pharmaceutically acceptable salt thereof, and at least one pharmaceutically acceptable excipient, for the manufacture of a medicament according to any one of embodiments 1h to 10h, wherein Compound (I) is administered in an amount of from 0.1 mg/day to 100 mg/day, in particular of from 1 mg/day to 50 mg/day, such as of from 2 mg/day to 10 mg/day, more particularly 5 mg/day.

Embodiment 12h: Use of a pharmaceutical composition comprising Compound (I), or pharmaceutically acceptable salt thereof, and at least one pharmaceutically acceptable excipient, for the manufacture of a medicament according to any one of embodiments 1h to 11h, wherein Compound (I), or pharmaceutically acceptable salt thereof, is administered to a sleepy insomniac shift work disorder patient or a sleepy non-insomniac shift work disorder patient.

Embodiment 13h: Use of a pharmaceutical composition comprising Compound (I), or pharmaceutically acceptable salt thereof, and at least one pharmaceutically acceptable excipient, for the manufacture of a medicament according to any one of embodiments 1h to 12h, wherein Compound (I), or pharmaceutically acceptable salt thereof, is administered orally.

Embodiment 14h: Use of a pharmaceutical composition comprising Compound (I), or pharmaceutically acceptable salt thereof, and at least one pharmaceutically acceptable excipient, for the manufacture of a medicament according to any one of the preceding embodiments, wherein shift work disorder is associated with night shift work, rotating shift work, evening shift work or early morning shift work, in particular, night shift work, such as permanent night shift work or rotating night shift work.

Embodiment 15h: Use of a pharmaceutical composition comprising Compound (I), or pharmaceutically acceptable salt thereof, and at least one pharmaceutically acceptable excipient, for the manufacture of a medicament according to any one of the preceding embodiments, wherein shift work is night shift work, rotating shift work, evening shift work or early morning shift work, in particular, night shift work, such as permanent night shift work or rotating night shift work.

Embodiments (i)

Embodiment 1j: A pharmaceutical combination comprising Compound (I), or pharmaceutically acceptable salt thereof, and at least one further pharmaceutical active ingredient, for the manufacture of a medicament for the treatment of shift work disorder.

Embodiment 2j: A pharmaceutical combination comprising Compound (I), or pharmaceutically acceptable salt thereof, and at least one further pharmaceutical active ingredient, for the manufacture of a medicament being an agent modulating circadian rhythm dysfunctions due to shift work.

Embodiment 3j: A pharmaceutical combination comprising Compound (I), or pharmaceutically acceptable salt thereof, and at least one further pharmaceutical active ingredient, for the manufacture of a medicament for the treatment of excessive sleepiness associated with shift work disorder.

Embodiment 4j: A pharmaceutical combination comprising Compound (I), or pharmaceutically acceptable salt thereof, and at least one further pharmaceutical active ingredient, for the manufacture of a medicament for promoting wakefulness in a shift work disorder patient.

Embodiment 5j: A pharmaceutical combination comprising Compound (I), or pharmaceutically acceptable salt thereof, and at least one further pharmaceutical active ingredient, for the manufacture of a medicament for the treatment of excessive sleepiness in a shift work disorder patient.

Embodiment 6j: A pharmaceutical combination comprising Compound (I), or pharmaceutically acceptable salt thereof, and at least one further pharmaceutical active ingredient, for the manufacture of a medicament for the treatment of cognitive function impairment associated with shift work disorder, in particular wherein cognitive function comprises cognitive domains selected from the group consisting of learning, psychomotor function, attention, sustained attention, working memory, episodic memory, executive function, auditory information processing speed, auditory information processing flexibility, and calculation ability; in a particular embodiment, wherein it comprises one or more cognitive domains selected from attention, sustained attention and psychomotor function; in another particular embodiment, wherein it comprises one or more cognitive domains selected from episodic memory, working memory and executive function.

Embodiment 7j: A pharmaceutical combination comprising Compound (I), or pharmaceutically acceptable salt thereof, and at least one further pharmaceutical active ingredient, for the manufacture of a medicament according to any one of embodiments 1j to 6j, wherein the further pharmaceutical active ingredient is a wakefulness-promoting agent.

Embodiment 8j: A pharmaceutical combination comprising Compound (I), or pharmaceutically acceptable salt thereof, and at least one further pharmaceutical active ingredient, for the manufacture of a medicament according to embodiment 7j, wherein the wakefulness-promoting agent is selected from the group consisting of modafinil, armodafinil, caffeine, methylphenidate, dextroamphetamine and sodium oxybate, or pharmaceutically acceptable salts thereof.

Embodiment 9j: A pharmaceutical combination comprising Compound (I), or pharmaceutically acceptable salt thereof, and at least one further pharmaceutical active ingredient, for the manufacture of a medicament according to embodiment 7j, wherein the wakefulness-promoting agent is modafinil or armodafinil, or pharmaceutically acceptable salts thereof.

Embodiment 10j: A pharmaceutical combination comprising Compound (I), or pharmaceutically acceptable salt thereof, and at least one further pharmaceutical active ingredient, for the manufacture of a medicament according to any one of embodiments 1j to 9j, wherein Compound (I) is administered in an amount of from 0.1 mg/day to 100 mg/day, in particular of from 1 mg/day to 50 mg/day, such as of from 2 mg/day to 10 mg/day, more particularly 5 mg/day.

Embodiment 11j: A pharmaceutical combination comprising Compound (I), or pharmaceutically acceptable salt thereof, and at least one further pharmaceutical active ingredient, for the manufacture of a medicament according to any one of embodiments 1j to 10j, wherein Compound (I), or pharmaceutically acceptable salt thereof, is administered to a sleepy insomniac shift work disorder patient or a sleepy non-insomniac shift work disorder patient.

Embodiment 12j: A pharmaceutical combination comprising Compound (I), or pharmaceutically acceptable salt thereof, and at least one further pharmaceutical active ingredient, for the manufacture of a medicament according to any one of embodiments 1j to 11j, wherein Compound (I), or pharmaceutically acceptable salt thereof, is administered orally.

Embodiment 13j: A pharmaceutical combination comprising Compound (I), or pharmaceutically acceptable salt thereof, and at least one further pharmaceutical active ingredient, for the manufacture of a medicament according to any one of the preceding embodiments, wherein shift work disorder is associated with night shift work, rotating shift work, evening shift work or early morning shift work, in particular, night shift work, such as permanent night shift work or rotating night shift work.

Embodiment 14j: A pharmaceutical combination comprising Compound (I), or pharmaceutically acceptable salt thereof, and at least one further pharmaceutical active ingredient, for the manufacture of a medicament according to any one of the preceding embodiments, wherein shift work is night shift work, rotating shift work, evening shift work or early morning shift work, in particular, night shift work, such as permanent night shift work or rotating night shift work.

General Terms

The term "shift work sleep disorder" or "shift work disorder" (SWSD or SWD), as used herein, is to be understood in relation to ICSD-3 diagnostic criteria, which are incorporated herein by reference.

As used herein, the term "shift work disorder patient", "patient diagnosed with shift work disorder" or "patient with shift work disorder" refers to a shift worker, such as a night shift worker, rotating shift worker, evening shift worker or early morning shift worker, wherein night shift work, evening shift work and early morning shift work are as described herein above. In particular, it refers to a night shift worker, such as a permanent night shift worker or a rotating night shift worker, diagnosed with SWD, for example, that presenting insomnia (i.e. alert insomniac), that presenting insomnia alongside excessive sleepiness (i.e. sleepy insomniac) or that presenting excessive sleepiness without insomnia (i.e. sleepy non-insomniac). As used herein "diagnosed with SWD" refers to confirmed diagnosis of SWD according to ICSD-3 criteria, which are incorporated herein by reference.

The term "insomnia", as used herein, refers, without limitation, to difficulty in initiating sleep, difficulty in maintaining sleep, waking up earlier than desired or having difficulty sleeping without intervention. In another embodiment, insomnia also refers to any sleep disturbance that happens, for example, during the conduct of a clinical study and that is reported as an adverse event, in this particular context, 'insomnia' refers to an event, not a diagnosis for a disorder, and for example, insomnia may be assessed by routine collection of adverse events (Czeisler et al 2005, 2009). Drug effect on sleep (e.g. on sleep quality) may also be assessed by PSG (Berry et al 2016).

The term "excessive sleepiness" (ES), as used herein, is to be understood in relation to standardized techniques, for example, based on ICSD-3 criteria, which are incorporated herein by reference. For example, excessive sleepiness may be assessed, as objective sleepiness, with the multiple sleep latency test [MSLT] (i.e. determining mean (±SD) MSLT latency), as recommended by relevant guidelines [Littner et al, Sleep, 2005, 28 (10), 113-121] or performed in other studies in shift work disorder patients [*N. Engl. J. Med.*, 2005, 353, 476-486 and in *Mayo Clin. Proc.*, 2009, 84 (11), 958-972]. In patients with SWD, the mean sleep latency in MSLT has been shown to be 3.2 minutes shorter than asymptomatic night workers (Gumenyuk et al, Chronobiology International, 29, 7, 2012, 928-936) and (at night) sleep latency in SWD patients with moderate to severe excessive sleepiness is <6 min (Drake, et al 2014, Gumenyuk, et al 2014, Czeisler, et al 2005, Czeisler, et al 2009). Alternatively, excessive sleepiness may be assessed, as subjective sleepiness, with the Karolinska Sleepiness Scale [KSS], which is a 9-point scale: 1. extremely alert, 2. very alert, 3. alert, 4. rather alert, 5. neither alert nor sleepy, 6. some signs of sleepiness, 7. Sleepy, but no effort to keep awake, 8. sleepy, but some effort to keep awake and 9. very sleepy, great effort to keep awake.

The term "wakefulness-promoting agent", as used herein, refers to an active agent capable of decreasing excessive sleepiness, for example, compared with excessive sleepiness observed without treatment.

The term "promoting wakefulness", as used herein, refers to decreasing excessive sleepiness, for example, compared with excessive sleepiness observed without treatment.

The term "sleep-inducing agent" refers to a compound capable of inducing sleep and/or improving the patient's quality of sleep.

The term "circadian rhythm dysfunctions", as used herein, refers to disruptions of the circadian rhythm (i.e. the "internal body clock" that regulates, for example, sleeping patterns, such as when to sleep and when to wake every 24 hours, wherein the normal circadian clock is set by the light-dark cycle over 24 hr). As used herein, the term "modulating" when used in reference to "circadian rhythm dysfunctions" refers to altering a physiological function (e.g. sleep-wake cycles; amount of wake and/or sleep, timing of wake and/or sleep) or behavior (e.g. alertness) that is regulated by the circadian timing system of a human, for example as measured by markers (e.g. in Gumenyuk et al., 2012.)

The term "cognitive function" as used herein refers, for example, to the ability to concentrate, remember things, make decisions, solve problems or think. Cognitive function comprises one or more cognitive domains selected from the group consisting of learning, psychomotor function, attention, sustained attention, working memory, episodic memory, executive function, auditory information processing speed, auditory information processing flexibility, and calculation ability. In one particular embodiment it comprises one or more cognitive domains selected from the group consisting of psychomotor function, attention, sustained attention, working memory, episodic memory, executive function, auditory information processing speed, auditory information processing flexibility, and calculation ability; more particularly, cognitive domains selected from the group consisting of psychomotor function, attention, sustained attention, working memory, episodic memory and executive function.

The term "cognitive function impairment" refers to a deficit in one or more of the cognitive domains relating to cognitive function, in particular a deficit in one or more cognitive domains selected from the group consisting of learning (i.e. learning impairment), psychomotor function (i.e. psychomotor function impairment), attention (i.e. attention impairment), sustained attention (i.e. sustained attention impairment), working memory (i.e. working memory impairment), episodic memory (i.e. episodic memory impairment), executive function (i.e. executive function impairment), auditory information processing speed (i.e. auditory information processing speed impairment), auditory information processing flexibility (i.e. auditory information processing flexibility impairment), and calculation ability (i.e. calculation ability impairment); for example, as measured by the Symbol Digit Modalities Test (SDMT, Smith, 1968), Paced Auditory Serial Addition Test (PASAT, Rao, 1990) and computerized tests (e.g. Cho, et al 2011, Grove, et al 2014). In one particular embodiment cognitive function impairment refers to attention impairment, sustained attention impairment or psychomotor function impairment. In another particular embodiment it refers to learning impairment, episodic memory impairment, working memory impairment or executive function impairment.

The term "impairment" as used herein refers to deficit, for example, diminished or reduced ability.

The term "attention" as used herein, refers to, but is not limited to, the ability to selectively concentrate on one aspect of the environment while ignoring other things.

The term "sustained attention" as used herein refers to, but is not limited to, the ability to maintain a consistent focus on a continuous activity or stimuli.

The term "executive function" as used herein, refers to, but is not limited to, the ability to plan, demonstrate cognitive flexibility and/or select relevant sensory information.

The term "episodic memory" as used herein refers to, but is not limited to, recollection-based recognition, or "remembering," such as remembering recently presented information or events.

The term "working memory" as used herein refers to, but is not limited to, the fast memory process for storage and retrieval, including processes required to retain incoming information in short-term memory before it is converted into long-term memory.

The term "learning" refers to, but is not limited to, the capability of obtaining new knowledge, or skills, for example, through instruction or experience.

The term "psychomotor function" refers to, but is not limited to, the coordination of a sensory or cognitive process and a motor activity as demonstrated by a subject through the completion of a task. For example, this can be demonstrated by a person required to acquire a target, engage the target effectively and accurately, and effectively address problems during target engagement.

The term "auditory information" refers to audio information, for example transmitted through voice or video communication.

The term "information processing speed" refers to, but is not limited to, the ability to maintain and manipulate information in the brain during a time period and to the velocity to process this information.

The term "auditory information processing speed", as used herein, refers to, but is not limited to, rate and pace of information processing received by auditory input.

The term "auditory information processing flexibility", as used herein, refers to, but is not limited to, the ability to mentally manipulate information received by auditory input.

The term "calculation ability", as used herein, refers to, but is not limited to, the ability to add consecutive numbers in one's head, for example, as the numbers are being read up.

The term "a therapeutically effective amount" of a compound of the present invention refers to an amount of a compound of the present invention that will elicit the biological or medical response of a subject, for example, ameliorate symptoms, alleviate conditions, slow or delay disease progression, etc. In another embodiment, the term "a therapeutically effective amount" refers to the amount of the compound of the present invention that, when administered to a subject, is effective to at least partially alleviate and/or ameliorate a condition, or a disorder or a disease.

As used herein, the term "subject" refers to a human (male or female).

As used herein, the term "patient" refers to a human who is diseased and would benefit from the treatment.

As used herein, a subject is "in need of" a treatment if such subject (patient) would benefit biologically, medically or in quality of life from such treatment.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. One aspect of the treatment is, for example, that said treatment should have a minimal adverse effect on the patient, e.g. the agent used should have a high level of safety, for example, without producing the side effects of the known treatment regimens.

The term "pharmaceutical composition" is defined herein to refer to a mixture or solution containing at least one active ingredient or therapeutic agent to be administered to a subject, in order to treat a particular condition (i.e. disease or condition or at least one of the clinical symptoms thereof) affecting the subject.

As used herein, the term "pharmaceutically acceptable excipient" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 22$^{nd}$ Ed. Mack Printing Company, 2013, pp. 1049-1070). Except insofar as any conventional carrier is incompatible with the active ingredient, its use in the therapeutic or pharmaceutical compositions is contemplated.

The terms "drug", "active substance", "active ingredient", "pharmaceutically active ingredient", "active agent" or "therapeutic agent" are to be understood as meaning a compound in free form or in the form of a pharmaceutically acceptable salt, in particular compounds of the type specified herein.

The term "combination" or "pharmaceutical combination" refers to either a fixed combination in one unit dosage form (e.g., capsule, tablet, caplets or particulates), non-fixed combination, or a kit of parts for the combined administration where a compound of the present invention and one or more combination partner (e.g. another drug as specified herein, also referred to as further "pharmaceutical active ingredient", "therapeutic agent" or "co-agent") may be administered independently at the same time or separately within time intervals, especially where these time intervals allow that the combination partners show a cooperative, e.g. synergistic effect. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "fixed combination" means that the active ingredients, e.g. the compound of the present invention and one or more combination partners, are both administered to a patient simultaneously in the form of a single entity or dosage. The term "non-fixed combination" means that the active ingredients, e.g. a compound of the present invention and one or more combination partners, are both administered to a patient as separate entities either simultaneously or sequentially with no specific time limits, wherein such administration provides therapeutically effective levels of the two compounds in the body of the patient.

The compound of the present invention may be administered separately, by the same or different route of administration, or together in the same pharmaceutical composition as the other agents. In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

As used herein, the term "a," "an," "the" and similar terms used in the context of the present invention (especially in the context of the claims) are to be construed to cover both the singular and plural unless otherwise indicated herein or clearly contradicted by the context.

The use of any and all examples, or exemplary language (e.g. "such as") provided herein is intended merely to better illuminate the invention and does not pose a limitation on the scope of the invention otherwise claimed.

As used herein, the compound of the invention, named Compound (I), as used herein above and below, is 1-(1-methyl-6-oxo-1,6-dihydropyridazin-3-yl)piperidin-4-yl 4-cyclobutylpiperazine-1-carboxylate, of formula:

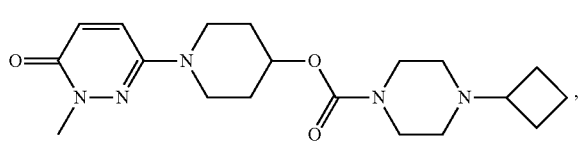 [SMILES: Cn1nc(N2CCC(OC(=O)N3CCN(C4CCC4)CC3)CC2)ccc1=O]

which can be e.g. prepared as described in WO2014/013469, e.g., in Example 1.5. WO2014/013469, which is incorporated herein by reference, also describes its in-vitro biological data, as per pages 40 to 42, as well as solid forms thereof, such as the free form in crystalline form, namely Ex. II. 1.1 (i.e. form A of the free form) and Ex. II. 1.2 (i.e. form B of the free form), as well as salts, for example the citrate salt (i.e. Ex. II. 2.1: form A of the citrate salt; Ex. II. 2.2: form B of the citrate salt), the hydrochloride salt (i.e. Ex. II. 4.1: form A of the hydrochloride salt; Ex. II. 4.2: form B of the hydrochloride salt), the fumarate salt (i.e. Ex. II. 3.1: form A of the fumarate salt; Ex. II. 3.2: form B of the fumarate salt), including preparations thereof. As used herein, 1-(1-methyl-6-oxo-1,6-dihydropyridazin-3-yl)piperidin-4-yl 4-cyclobutylpiperazine-1-carboxylate, or a pharmaceutically acceptable salt thereof, refers in particular to the free form, such as the form A or B of the free form, the citrate salt, such as the form A or B of the citrate salt, the hydrochloride salt, such as the form A or B of the hydrochloride salt, the fumarate salt, such as the form A or B of the fumarate salt. In one embodiment the compound of the invention 1-(1-methyl-6-oxo-1,6-dihydropyridazin-3-yl)piperidin-4-yl 4-cyclobutylpiperazine-1-carboxylate is in the form A of the free form. In a another embodiment. compound of the invention 1-(1-methyl-6-oxo-1,6-dihydropyridazin-3-yl)piperidin-4-yl 4-cyclobutylpiperazine-1-carboxylate is in the form B of the free form.

In one embodiment, 1-(1-methyl-6-oxo-1,6-dihydropyridazin-3-yl)piperidin-4-yl 4-cyclobutylpiperazine-1-carboxylate is also intended to represent isotopically labeled forms. Isotopically labeled compounds have structures depicted by the formulas except that one or more atoms are replaced by an atom having a selected atomic mass or mass number. Isotopes that can be incorporated into the compound of the invention include, for example, isotopes of hydrogen, namely the compound of formula:

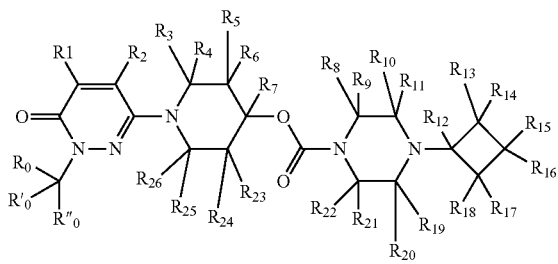

wherein each $R_0$, $R'_0$, $R''_0$, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$ and $R_{26}$ is independently selected from H or deuterium; provided that there is at least one deuterium present in the compound. In other embodiments there are multiple deuterium atoms present in the compound. In on embodiment, for example, R0, R'0 and R"0 are deuterium atoms. In another embodiment, for example, R12 is a deuterium atom. In yet another embodiment, for example R1 and R2 are deuterium. In still a further embodiment, for example, R13 to R18 are deuterium atoms.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of the compound of the invention. The concentration of deuterium, may be defined by the isotopic enrichment factor. The term "isotopic enrichment factor" as used herein means the ratio between the isotopic abundance and the natural abundance of a specified isotope. If a substituent in the compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into the compound of the invention include isotopes of hydrogen, other than deuterium, carbon, nitrogen, oxygen, and fluorine such as $^3$H, $^{11}$C, $^{13}$C, $^{14}$C, $^{15}$N, $^{18}$F respectively. Accordingly it should be understood that the invention includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. The isotopically-labeled compounds can generally be prepared by conventional techniques known to those skilled in the art or by processes analogous to those described preparation of the compound of the invention by using an appropriate isotopically-labeled reagents in place of the non-labeled reagent previously employed.

As used herein, the terms "free form" or "free forms" refers to the compound in non-salt form, such as the base free form or the acid free form of a respective compound, e.g. the compounds specified herein (e.g. Compound (I) or further pharmaceutical active ingredient, such as a wakefulness-promoting agent, for example, as defined herein).

As used herein, the terms "salt", "salts" or "salt form" refers to an acid addition or base addition salt of a respective compound, e.g. the compounds specified herein (e.g. Compound (I) or further pharmaceutical active ingredient, such as a wakefulness-promoting agent, for example, as defined herein). "Salts" include in particular "pharmaceutically acceptable salts". The term "pharmaceutically acceptable salts" refers to salts that retain the biological effectiveness and properties of the compounds and, which typically are not biologically or otherwise undesirable. The compounds, as specified herein (e.g. Compound (I) or further pharmaceutical active ingredient, such as a wakefulness-promoting agent, for example, as defined herein), may be capable of forming acid and/or base salts by virtue of the presence of amino and/or carboxyl groups or groups similar thereto. The compound of the invention is capable of forming acid addition salts by virtue of the presence of amino group similar thereto, such as the citrate salt, hydrochloride salt, fumarate salt, adipate salt, maleate salt or sebacate salt thereof; in particular the citrate salt, hydrochloride salt and fumarate salt thereof. Thus, as used herein, the term pharmaceutically acceptable salt of 1-(1-methyl-6-oxo-1,6-dihydropyridazin-3-yl)piperidin-4-yl 4-cyclobutylpiperazine-1-carboxylate means a pharmaceutically acceptable acid addition salt of 1-(1-methyl-6-oxo-1,6-dihydropyridazin-3-yl)piperidin-4-yl 4-cyclobutylpiperazine-1-carboxylate.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

Pharmaceutically acceptable salts can be synthesized from a basic or acidic moiety, by conventional chemical methods. Generally, such salts can be prepared by reacting the free acid forms of the compound with a stoichiometric amount of the appropriate base (such as Na, Ca, Mg, or K hydroxide, carbonate, bicarbonate or the like), or by reacting the free base form of the compound with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", $22^{nd}$ edition, Mack Publishing Company (2013); and in "Handbook of Pharmaceutical Salts: Properties, Selection, and Use" by Stahl and Wermuth (Wiley-VCH, Weinheim, 2011, $2^{nd}$ edition).

The compounds specified herein (e.g. Compound (I) or further pharmaceutical active ingredient, such as a wakefulness-promoting agent, for example, as defined herein) can be administered by conventional route, in particular orally, such as in the form of tablets, capsules, caplets or particulates, which can be manufactured according to pharmaceutical techniques as known in the art (for example in "Remington Essentials of Pharmaceutics, 2013, $1^{st}$ Edition, edited by Linda Felton, published by Pharmaceutical Press 2012, ISBN 978 0 85711 105 0; in particular Chapter 30), wherein pharmaceutical excipients are, for example, as described in "Handbook of Pharmaceutical Excipients, 2012, $7^{th}$ Edition, edited by Raymond C. Rowe, Paul J. Sheskey, Walter G. Cook and Marian E. Fenton, ISBN 978 0 85711 027 5".

The pharmaceutical composition or combination of the present invention can be in a unit dosage form (e.g. tablet, capsule, caplet or particulate) comprising an amount ranging of from 0.1 mg to 100 mg, in particular of from 1 mg to 50 mg, such as 2 mg to 10 mg, more particularly 5 mg, of Compound (I) (referring to an amount of the free form of Compound (I), and if a salt thereof is used the amount will be adapted accordingly; in particular Compound (I) is in the free form, such as the form A of the free form or the form B of the free form). For the above-mentioned uses/treatment methods the appropriate dosage may vary depending upon a variety of factors, such as, for example, the age, weight, sex, the route of administration or salt employed. In patients with, for example, of from 50-70 kg body weight, an indicated daily dosage is of from 0.1 mg to 100 mg, in particular of from 1 mg to 50 mg, such as 2 mg to 10 mg, more particularly 5 mg, of Compound (I) (referring to an amount of the free form of Compound (I), and if a salt thereof is used the amount will be adapted accordingly; in particular Compound (I) is in the free form, such as the form A of the free form or the form B of the free form).

REFERENCES

Rao S M. A Manual for the Brief Repeatable Battery of Neuropsychological Tests in Multiple Sclerosis. Milwaukee, Wis, USA: Medical College of Wisconsin; 1990.

Smith, A. (1968). The symbol-digit modalities test: a neuropsychologic test of learning and other cerebral disorders. In J. Helmuth (Ed.), Learning disorders (pp. 83-91). Seattle: Special Child Publications.

EMA (2010) European Medicines Agency (2010) Press release: European Medicines Agency recommends restricting the use of modafinil.

Guy W (1976) ECDEU Assessment Manual for Psychopharmacology.

Akerstedt T and Gillberg M (1990) Subjective and objective sleepiness in the active individual p. 29-37.

Berry R B, Brooks R, Gamaldo C E, Harding S M, Lloyd R M, Marcus C L and Vaughn B V for the American Academy of Sleep Medicine. The AASM Manual for the Scoring of Sleep and Associated Events: Rules, Terminology and Technical Specifications, Version 2.3. www.aasmnet.org. Darien, Ill.: American Academy of Sleep Medicine, 2016.

Cho W, Maruff P, Connell J, et al. (2011) Additive effects of a cholinesterase inhibitor and a histamine inverse agonist on scopolamine deficits in humans. Psychopharmacology (Berl), 218(3):513-24.

Czeisler C A, Walsh J K, Roth T, et al. (2005) Modafinil for excessive sleepiness associated with shift-work sleep disorder. N Engl J Med, 353:476-86.

Czeisler C A, Walsh J K, Wesnes K A, et al. (2009) Armodafinil for treatment of excessive sleepiness associated with shift work disorder: a randomized controlled study. Mayo Clin Proc, 84:958-72.

Drake C, Gumenyuk V, Roth T, et al. (2014) Effects of armodafinil on simulated driving and alertness in shift work disorder. Sleep, 37:1987-94.

Drake C L, Roehrs T, Richardson G, et al. (2004) Shift work sleep disorder: prevalence and consequences beyond that of symptomatic day workers. Sleep, 27:1453-62.

Grove R A, Harrington C M, Mahler A, et al. (2014) A randomized, double-blind, placebo-controlled, 16-week study of the H3 receptor antagonist, GSK239512 as a monotherapy in subjects with mild-to-moderate Alzheimer's disease. Curr Alzheimer Res, 11(1):47-58.

Gumenyuk V, Howard R, Roth T, et al. (2014) Sleep loss, circadian mismatch, and abnormalities in reorienting of attention in night workers with shift work disorder. Sleep, 37:545-56.

Schwartz J R and Roth T (2006) Shift work sleep disorder: burden of illness and approaches to management. Drugs, 66:2357-70.

Howard R, Roth T, Drake C L (2014) The effects of armodafinil on objective sleepiness and performance in a shift work disorder sample unselected for objective sleepiness. J Clin Psychopharmacol p. 369-73.

Muehlbach M J, Walsh J K (1995) The effects of caffeine on simulated night-shift work and subsequent daytime sleep. Sleep p. 22-9.

Walsh J K, Randazzo A C, Stone K L, et al. (2004) Modafinil improves alertness, vigilance, and executive function during simulated night shifts. Sleep p. 434-9.

Wesensten N J, Killgore W D, Balkin T J (2005) Performance and alertness effects of caffeine, dextroamphetamine, and modafinil during sleep deprivation. J Sleep Res p. 255-66.

Kiviranta T, Tuomisto L and Airaksinen E M (1994) Diurnal and age-related changes in cerebrospinal fluid tele-methylhistamine levels during infancy and childhood. Pharmacol Biochem Behav, 49:997-1000.

Gumenyuk V, Roth T and Drake C L (2012) Circadian phase, sleepiness, and light exposure assessment in night workers with and without shift work disorder. Chronobiol Int, 29:928-36.

Iannone R, et al (2010) Acute alertness-promoting effects of a novel histamine subtype-3 receptor inverse agonist in healthy sleep-deprived male volunteers. Clin. Pharmacol. Ther. p. 831-839.

Esbenshade T A, et al (2208) The histamine H3 receptor: an attractive target for the treatment of cognitive disorders. Br. J. Pharmacol. 154(6):1166-81.

Abreviations

ICSD=International Classification of Sleep Disorders
SWD or SWSD=Shift Work Disorder or Shift Work Sleep Disorder
SDMT=Symbol Digit Modalities Test [Smith, 1968],
PASAT=Paced Auditory Serial Addition Test [Rao, 1990]
MSLT=Multiple Sleep Latency Test [Littner et al, *Sleep*, 2005, 28 (10), 113-121]
CGI-S=Clinical Global Impression-Severity scale [CGI-S, Guy 1976]
KSS=Karolinska Sleepiness Scale [Akerstedt and Gillberg 1990]
PSG=polysomnography [Berry et al 2016]
LCMS or LC-MS=Liquid chromatography-mass spectrometry
PK=pharmacokinetic(s)
HA=histamine
hr(s)=hour(s)
tMeHA=tele-methylhistamine
CSF=cerebrospinal fluid
PD=pharmacodynamics(s)
FIH=First-in-human
HV=healthy volunteer(s)
ECG=electrocardiogram
AE=adverse event
SAE=serious adverse event
EOS=end of study?
SD=standard deviation
CV=coefficient of variation
CI=confidence interval
ANOVA=analysis of variance
min=minutes

EXAMPLES

The following Examples serve to illustrate the invention without limiting the scope thereof.
Methods:

Example 1

Study Design

A randomized, double-blind, placebo-controlled, parallel group, exploratory study of single oral doses of Compound (I) (free form) was conducted in healthy volunteers (HVs) to investigate the pharmacodynamic effect of Compound (I) on the release of neurotransmitters in the brain. A total of 16 subjects were enrolled into the study, which was part of a first-in-human (FIH) study. Subjects were randomized in a 1:1 ratio to receive either a single dose of Compound (I) or placebo.

On study Day 1 in the afternoon (approximately at 16:00), the HVs underwent lumbar puncture and a spinal catheter was placed for repeated cerebrospinal fluid (CSF) sampling. The spinal catheter was placed under strict surgical aseptic conditions, as per best practice standards, by a board certified anesthesiologist. Two CSF samples were collected before administration of the study drug (Compound (I) or placebo). Study drug was administered in the evening (approximately at 18:00). Thereafter, 10 more CSF samples were collected during 16 hrs following drug administration. The exact timing of sampling (0.5, 1, 1.5, 2, 3, 4, 6, 8, 12 and 16 hr post dose). During the same period, blood samples were also collected for pharmacokinetic (PK) analysis. The subjects remained at bed rest during the CSF sampling procedure and for about 24 hr afterwards. The following safety precautions were taken: (1) proper hydration of the subjects was ensured; (2) the catheter insertion site was assessed on a regular basis for early signs of local infection or CSF leakage; (3) prophylactic interventions/treatments to reduce the risk of venous thrombosis was considered by the Investigator.

The dose of Compound (I) (free form) administered to the subjects was 100 mg. Safety, tolerability and PK assessments were made up to 72 hr post dose. Subjects were allowed to leave the study center on Study Day 4 at the discretion of the Investigator, if there were no prohibitive safety findings. The subjects were asked to return to the study site for the study completion evaluation. Safety assessments included physical examinations, electrocardiograms (ECGs), vital signs, standard clinical laboratory evaluations (hematology, blood chemistry, and urinalysis), adverse events (AEs) and serious adverse events (SAEs) monitoring.
Biomarker Analysis:

Biomarkers related to pharmacodynamic (PD) effect of Compound (I) (e.g. histamine [HA], tele-methylhistamine [tMeHA]) were measured in the CSF using LC-MS method.

LC-MS conditions for histamine (%=percent by volume): Acquity Binary Solvent Manager/Applied Biosystems API 5000; Mobile Phase A: acetonitrile, B: 10 mM ammonium formate pH3; Gradient: 10% A for 0.25 min, increase to 15% A within 0.25 min, increase to 25% A within 4 min, increase to 90% A within 0.10 min, 90% A for 0.9 min, back to 10% A within 0.10 min, 10% A for 2.40 min; Run time: 8 min; Flow rate: 0.35 mL/min; Analytical column: Acquity BEH C18, 150×2.1 mm, 1.7 µm; Temperature: 30° C. The desired compound histamine LC-MS: Rt=3.85 min, m/z 246 $(M+H)^+$ LC-MS conditions for tele-methyl-histamine (%=percent by volume): Acquity Binary Solvent Manager/Applied Biosystems API 5000; Mobile Phase A: acetonitrile, B: 10 mM ammonium formate pH9; Gradient: 15% A for 0.25 min, increase to 25% A within 4.75 min, increase to 90% A within 0.10 min, 90% A for 0.50 min, back to 15% A within 0.10 min, 15% A for 0.60 min; Run time: 6.3 min; Flow rate: 0.65 mL/min; Analytical column: Acquity BEH C18, 150×2.1 mm, 1.7 µm; Temperature: 70° C. The desired compound tele-methyl-histamine LC-MS: Rt=4.66 min, m/z 260 $(M+H)^+$ Compound (I) can induce histamine release in a subject and thereby promote wakefulness. The tMeHA is the direct breakdown product of HA and can thus be used as a marker for HA release. In animals, the half-life of HA is about 20 minutes. Therefore HA is not an ideal mechanistic PD marker for Compound (I). due to its short half-life. HA is turned into the inactive metabolite tMeHA by the enzyme histamine-N-methyltransferase. tMeHA in the brain undergoes oxidative deamination through a monoamine oxidase (MAO-B) and an aldehyde dehydrogenase and finally t-methyl-imidazoleacetic acid is formed, a process that has a half-life of about 2-3 hrs. Due to its slower breakdown, tMeHA was expected to be a more useful PD marker of Compound (I) activity than HA itself.

Statistical Analysis:

The effect of Compound (I) on CSF biomarkers was assessed using mixed models for repeated measures (MMRM). These parameters were log transformed and analyzed using a model including treatment and timepoint, the treatment*timepoint interaction term, and log transformed baseline as fixed effects. An unstructured residual covariance matrix within subjects was considered as desirable, but an alternative covariance structure (autoregressive) was used due to a lack of fit. The mean difference versus placebo (and its 90% CI) was calculated at each dose level. These were back-transformed to give a geometric ratio (and its 90% CI) between each dose and placebo.

Subjects: The study population comprised of male and female (of non-child bearing potential) healthy volunteers (HVs) 18-55 years of age. Subjects weighed at least 50 kg to participate in the study, and had a body mass index (BMI) within the range of 18-29.9 kg/m2. BMI=Body weight (kg)/[Height (m)]2. Subjects were able to communicate well with the Investigator, to understand and comply with the requirements of the study. Subjects were in good health as determined by medical history, physical examination, vital signs, electrocardiogram, electroencephalogram (resting state and hyperventilation and intermittent photic stimulation paradigm) and laboratory tests. Subjects, who in their medical history had certain conditions that might represent a risk during treatment with Compound (I) or for lumbar catheter placement were excluded from the study.

Results:

Mean CSF HA levels decreased for about 6 to 8 hrs post dose (during the night) in both treatment groups but returned to approximately baseline levels at the last measurement point (morning of Day 2). The time course of HA in CSF reflects the well-known diurnal variation of brain HA levels (Kiviranta et al 1994). No clear trend of a difference between the mean CSF HA levels was observed between Compound (I) (free form, 100 mg, single unit dose) and placebo groups.

TABLE

Treatment comparison of model adjusted geometric mean ratio to baseline of histamine in CSF
Parameter: Histamine(pg/mL)

| Hrs post-dose Treatment | Geometric Mean | Comparison of treatment vs placebo | | |
|---|---|---|---|---|
| | | Estimate | (90% CI) | P-value |
| 0.5, 100 mg | 1.27 | 1.16 | (0.85, 1.58) | 0.426 |
| Placebo | 1.09 | | | |
| 1.0, 100 mg | 1.09 | 0.96 | (0.70, 1.31) | 0.812 |
| Placebo | 1.14 | | | |
| 1.5, 100 mg | 0.95 | 0.97 | (0.71, 1.33) | 0.882 |
| Placebo | 0.98 | | | |
| 2.0, 100 mg | 1.02 | 0.99 | (0.71, 1.39) | 0.967 |
| Placebo | 1.03 | | | |
| 3.0, 100 mg | 1.01 | 1.15 | (0.83, 1.58) | 0.482 |
| Placebo | 0.88 | | | |
| 4.0, 100 mg | 0.73 | 0.79 | (0.58, 1.08) | 0.211 |
| Placebo | 0.93 | | | |
| 6.0, 100 mg | 0.63 | 0.64 | (0.46, 0.88) | 0.022 |
| Placebo | 0.98 | | | |
| 8.0, 100 mg | 0.83 | 1.14 | (0.82, 1.58) | 0.521 |
| Placebo | 0.73 | | | |
| 12.0, 100 mg | 0.84 | 1.14 | (0.81, 1.58) | 0.527 |
| Placebo | 0.74 | | | |
| 16.0, 100 mg | 0.92 | 0.82 | (0.59, 1.15) | 0.333 |
| Placebo | 1.12 | | | |

Mean CSF tMeHA level declined from baseline for about 12 hr post dose in the placebo group and showed an upward tendency towards baseline at the last measurement point. In contrast, mean tMeHA level was increased compared to baseline after Compound (I) administration for about 10 hrs, then returned to baseline. For the entire observation period, mean ratio of tMeHA to baseline was higher in the Compound (I) group than in the placebo group. The between group difference was statistically significant at 1.5 hrs post dose and at all subsequent sampling points.

TABLE

Treatment comparison of model adjusted geometric mean ratio to baseline for of tele-methylhistamine in CSF
Parameter: tele-methylhistamine (pg/mL)

| Hours post-dose | Treatment | Geometric Mean | Comparison of treatment vs placebo | | |
|---|---|---|---|---|---|
| | | | Estimate | (90% CI) | P-value |
| 0.5 | 100 mg | 1.01 | 1.02 | (0.74, 1.40) | 0.917 |
| | Placebo | 0.99 | | | |
| 1.0 | 100 mg | 1.17 | 1.10 | (0.80, 1.50) | 0.629 |
| | Placebo | 1.07 | | | |
| 1.5 | 100 mg | 1.30 | 1.39 | (1.01, 1.90) | 0.086 |
| | Placebo | 0.94 | | | |
| 2.0 | 100 mg | 1.73 | 1.77 | (1.23, 2.55) | 0.011 |
| | Placebo | 0.98 | | | |
| 3.0 | 100 mg | 1.64 | 1.88 | (1.35, 2.64) | 0.002 |
| | Placebo | 0.87 | | | |
| 4.0 | 100 mg | 1.21 | 1.63 | (1.18, 2.26) | 0.014 |
| | Placebo | 0.74 | | | |
| 6.0 | 100 mg | 1.59 | 1.85 | (1.32, 2.59) | 0.003 |
| | Placebo | 0.86 | | | |
| 8.0 | 100 mg | 1.20 | 2.14 | (1.51, 3.04) | <0.001 |
| | Placebo | 0.56 | | | |
| 12.0 | 100 mg | 0.79 | 2.45 | (1.75, 3.44) | <0.001 |
| | Placebo | 0.32 | | | |
| 16.0 | 100 mg | 1.04 | 1.57 | (1.10, 2.22) | 0.036 |
| | Placebo | 0.66 | | | |

Conclusions

Compound (I) induced a robust increase in mean tMeHA level in CSF, providing direct evidence of pharmacological activity of the compound in human brain. In contrast, mean tMeHA concentration declined during the night in the placebo group, which probably reflects diurnal rhythm of the biomarker. No treatment response was detected in mean HA levels, which might be due to the short half-life of HA in CSF, making the measurement of this neurotransmitter very challenging.

Concentration of HA in the CSF is low during the night, as HA release shows a distinct diurnal variation (Kiviranta et al 1994). Above results indicate that Compound (I) can increase HA release in the human brain during night. Increased HA release can promote wakefulness (Iannone, 2010) and improve cognition in humans (Esbenshade, 2008; Cho, 2011), which can be beneficial for Shift Work Disorder (SWD) patients, who suffer from excessive sleepiness (ES) and impaired cognitive function during their night or early morning shift, which falls outside of the regular hours of wakefulness.

Example 2

Study Design

This is a randomized, double-blind, placebo controlled, crossover, multi-center Proof of Concept (PoC) study with in-house simulated laboratory night shifts in patients with SWD. This non-confirmatory study includes two treatment arms: Compound (I) (free form. 5 mg; single unit dosage form) and placebo.

The study utilizes a 2×2 crossover design, with two treatment periods and two sequences as shown in FIG. 1. A total of 46 subjects are randomized in this study. All subjects receive both treatments (Compound (I) and placebo), one in each treatment period, with the order of treatment being randomized.

An initial screening period includes screening for eligibility followed by two weeks (14 consecutive days) of actigraphy (outpatient) to confirm SWD diagnosis according to ICSD-3 criteria, which are incorporated herein by reference. Subsequently daytime sleep PSG and nighttime MSLT are performed in the sleep lab on consecutive days that follow at least 3 night shifts worked by the patient to exclude any other sleep disorder and estimate the severity of objective sleepiness, respectively. A baseline prior to each treatment period includes three days of outpatient actigraphy monitoring and other baseline assessments performed as an out-patient visit. The baseline periods are timed such that they correspond to night shifts worked by the subjects in their regular work environment. Thus subjects enter the sleep laboratory clinical site for the treatment periods after at least three consecutive nights of working a night shift schedule. Each treatment period comprises two nights of treatment and concomitant assessments and one day of recovery sleep in between (Day 2). Stay at the study center for recovery sleep on Day 3 is optional.

Assessments are identical in both treatment periods. After at least three consecutive nights of normal night shift work schedule, subjects enter the sleep laboratory clinical site for their daytime period of sleep (Day 1) starting at approximately 10:00. No sleep assessment is performed on Day 1, but other baseline assessments are performed as specified in the assessment schedule.

Sleep lab assessments are done for the first treatment period, which are then repeated in the second treatment period. On Night 1, baseline cognitive tests and safety assessments are performed between 18:00 and 20:30. Cognitive function may be measured by the Symbol Digit Modalities Test (SDMT, Smith, 1968), by the Paced Auditory Serial Addition Test (PASAT, Rao, 1990) and by computerized tests (e.g. Cho, et al 2011, Grove, et al 2014). The subjects receive the first dose of assigned drug at approximately 21:00, and then perform a series of assessments repeated at regular intervals throughout the night. Wakefulness is assessed using the KSS and the MSLT at 1:30, 3:30, 5:30 and 7:30. Computerized tests and a paper and pencil test, the SDMT, are performed at 0:30, 2:30, 4:30 and 6:30 to assess effect on psychomotor function, attention and sustained attention. In addition, the subjects perform up to three computerized tests and two paper and pencil tests (PASAT and SDMT) to assess working memory, executive function, episodic memory, auditory information processing speed, auditory information processing flexibility, and calculation ability at 4:30. Subjects are not allowed to nap during the assessment nights outside the MSLT exams. They are continuously supervised by site personnel to make sure they stay awake during the test nights.

Subjects remain in the clinic for recovery sleep during Day 2 starting at approximately 10:00, and undergo PSG to assess daytime sleep. Total time spent in bed on Day 2 should be similar to and no more than 30 min longer than on Day 1. In parallel to PSG, sleep is also investigated using up to two portable devices, one wearable and another that is placed under the mattress. Subjects are also requested to fill out a sleep diary upon waking on the days specified in the assessment schedule.

Subjects receive the second dose of assigned drug at approximately 21:00 on Night 2. Subjects then repeat all of the same assessments as done on Night 1 at approximately the same clocktime. In addition, global clinical impression of sleepiness is also assessed after the 7:30 test session using the Clinical Global Impression-Improvement (CGI-I) sub-scale (Guy 1976). Once all assessments on the morning of Day 3 have been completed, subjects can either remain in the clinic for Day 3 recovery sleep, or are provided with safe transportation home for recovery sleep.

Sparse PK sampling is done over the two day study period. Treatment periods are separated by a wash-out of 1-3 weeks, depending on each subject's night shift work schedule. After both treatment periods have been completed subjects undergo Study Completion evaluations and are discharged from the study.

Statistical Model and Method of Analysis

Primary Variable:

The mean of sleep latency scores is the primary variable of this study.

Each subject undergoes a sleep latency test assessment at each period, at approximately 1:30, 3:30, 5:30 and 7:30 in Day 2 (Night 1) and Day 3 (Night 2). The mean value of all the sleep latencies from a subject within a period is defined as mean sleep latency score for that subject for that period.

Statistical Analysis of Primary Variable:

Mean sleep latency score data is analyzed using a mixed effect ANOVA model with treatment and period as fixed effects and subject as a random effect. Least square estimates for each treatment and treatment difference (Compound (I) vs placebo) along with 95% confidence interval are reported. In studies with short treatment duration in SWD patients or healthy shift workers the usual approach is to compare post-dose conditions and not change from baseline (Howard, Roth and Drake 2014; Drake, et al 2014; Muehlbach and Walsh 1995; Walsh, et al 2004; Wesensten, Killgore and Balkin 2005). The reason for this approach is the high variability in MSLT (average of at least three tests is needed as baseline) and that baseline and post-dose MSLT results needs to be time matched, as MSLT results depend on circadian rhythm.

The following assessments are performed:

a. Statistical significance: One sided (superiority) p-value of Compound (I) vs placebo from above fitted ANOVA model is reported.

b. Estimate of treatment difference (Compound (I) vs Placebo) is reported.

Graphical display: For a thorough investigation of sleep latency time profiles, data from Compound (I) and placebo are superimposed using suitable graphical tools like boxplot or arithmetic mean (SD) statistics.

Descriptive Summary:

Sleep latency data are summarized by treatment and time point. Summary statistics like N, mean, SD, CV, and range are reported.

Secondary Endpoints:

Safety and PK are secondary endpoints for this study.

Secondary Variables:

Safety: Standard safety endpoints such as adverse events, vital signs, hematology, blood chemistry, and urinalysis. Results of daytime PSG (i.e. objective measurements of sleep, such as measurements of total sleep time, sleep efficiency, sleep onset latency, wake after sleep onset, REM onset latency, number of awakenings).

PK: Compound (I) plasma concentration

Sample Size Calculation

A total of 46 subjects are enrolled in this study.

Based on Czeisler (2005) et al a 2 minutes increase in primary endpoint for SWD patients compared to placebo is considered to be the 'true effect'. Furthermore a SD of 4 minutes and a 20% drop out rate is used based on other sleep disorder study experience.

Efficacy Criteria:
  a. Statistical significance: A significant increase compared to placebo in sleep latency characterized by p-value <0.1; and
  b. At least 1 minute increase in MSLT sleep latency compared to placebo characterized by an estimated mean difference of >1 minute Sample size is evaluated based on a simulation exercise with an ANOVA model with treatment and period as fixed effects.

The invention claimed is:

1. A method for treating excessive sleepiness associated with shift work disorder, in a subject, in need thereof, comprising administering to said subject an effective amount of 1-(1-methyl-6-oxo-1,6-dihydropyridazin-3-yl)piperidin-4-yl 4-cyclobutylpiperazine-1-carboxylate, or pharmaceutically acceptable salt thereof.

2. A method for promoting wakefulness in a shift work disorder patient, in need thereof, comprising administering to said shift work disorder patient an effective amount of 1-(1-methyl-6-oxo-1,6-dihydropyridazin-3-yl)piperidin-4-yl 4-cyclobutylpiperazine-1-carboxylate, or pharmaceutically acceptable salt thereof.

3. The method according to claim 1, wherein said 1-(1-methyl-6-oxo-1,6-dihydropyridazin-3-yl)piperidin-4-yl 4-cyclobutylpiperazine-1-carboxylate, or pharmaceutically acceptable salt thereof, is administered in the form of a pharmaceutical composition further comprising at least one pharmaceutically acceptable excipient.

4. The method according to claim 1, wherein said 1-(1-methyl-6-oxo-1,6-dihydropyridazin-3-yl)piperidin-4-yl 4-cyclobutylpiperazine-1-carboxylate, or pharmaceutically acceptable salt thereof, is administered in combination with one or more further pharmaceutical active ingredient.

5. The method according to claim 4, wherein said further pharmaceutical active ingredient is a wakefulness-promoting agent.

6. The method according to claim 5, wherein said wakefulness-promoting agent is selected from the group consisting of modafinil, armodafinil, caffeine, methylphenidate, dextroamphetamine and sodium oxybate, or pharmaceutically acceptable salts thereof.

7. The method according to claim 5, wherein said wakefulness-promoting agent is modafinil or armodafinil, or pharmaceutically acceptable salts thereof.

8. The method according to claim 1, wherein said 1-(1-methyl-6-oxo-1,6-dihydropyridazin-3-yl)piperidin-4-yl 4-cyclobutylpiperazine-1-carboxylate is administered in an amount of from 0.1 mg/day to 100 mg/day.

9. The method according to claim 1, wherein said 1-(1-methyl-6-oxo-1,6-dihydropyridazin-3-yl)piperidin-4-yl 4-cyclobutylpiperazine-1-carboxylate, or pharmaceutically acceptable salt thereof, is administered to a sleepy insomniac shift work disorder patient or a sleepy non-insomniac shift work disorder patient.

10. The method according to claim 1, wherein said 1-(1-methyl-6-oxo-1,6-dihydropyridazin-3-yl)piperidin-4-yl 4-cyclobutylpiperazine-1-carboxylate, or pharmaceutically acceptable salt thereof, is administered orally.

11. The method according to claim 1, wherein said shift work disorder is associated with night shift work, rotating shift work, evening shift work or early morning shift work.

12. The method according to claim 1, wherein said shift work is night shift work, rotating shift work, evening shift work or early morning shift work, in particular, night shift work, such as permanent night shift work or rotating night shift work.

* * * * *